United States Patent [19]

Vaillancourt

[11] Patent Number: 4,636,200

[45] Date of Patent: Jan. 13, 1987

[54] INTUBATING DEVICE

[75] Inventor: Vincent L. Vaillancourt, Livingston, N.J.

[73] Assignee: Chesebrough-Pond's Inc., Greenwich, Conn.

[21] Appl. No.: 776,774

[22] Filed: Sep. 17, 1985

[51] Int. Cl.[4] .................... A61M 25/00

[52] U.S. Cl. .................... 604/170; 604/280; 128/657

[58] Field of Search .................... 604/95, 170, 280–283, 604/270; 128/656–658, 772

[56] References Cited

U.S. PATENT DOCUMENTS

| | | | |
|---|---|---|---|
| 3,572,333 | 3/1971 | Hubert | 604/170 |
| 3,757,768 | 9/1973 | Kline | 604/95 X |
| 4,388,076 | 6/1983 | Waters | 604/170 X |
| 4,390,017 | 6/1983 | Harrison et al. | 604/270 |
| 4,496,347 | 1/1985 | MacLean et al. | 604/164 |
| 4,559,046 | 12/1985 | Groshong et al. | 604/170 |

*Primary Examiner*—Dalton L. Truluck

*Attorney, Agent, or Firm*—Morgan & Finnegan

[57] ABSTRACT

This invention relates to a new and improved intubating device and more particularly to an intubating device wherein it can be determined that the metal stylet is properly positioned by the aspiration process without removal and subsequent reinsertion of the metal stylet. The intubating device consists of an assembly of a feeding tube in assembled relationship with a tube connector. A stylet holder having a stylet attached thereto is adapted to be assembled in telescoping relationship with the flexible feeding tube. The metal stylet is made of twisted metal wire so as to provide a rough exterior. The metal stylet is embedded in a blind hole in the hub of the stylet holder and is offset from the liquid passageway.

3 Claims, 3 Drawing Figures

INTUBATING DEVICE

FIELD OF THE INVENTION

The invention relates to intubating devices and more particularly to a new and improved intubating device of the type that permits aspiration of gastric juices to determine if the device is properly positioned.

BACKGROUND OF THE INVENTION

Intubating or naso-gastric devices in one form or another have been known for centuries and are used to provide nourishment to human patients, many of whom may be comatose or semi-comatose, who are otherwise unable to take nourishment. For example, following surgery a patient may need such a device for a brief period of time during recovery. Typically, such devices consist of four parts or elements, namely, a flexible feeding tube for conveying nourishment, a stylet preferably made of metal for positioning the feeding tube, a Bolus tube or weight for positioning the feeding tube in the duodena or jejunal and a connector for attachment of a supply of nourishment to the feeding tube.

In the use of intubating or naso-gastric devices it is, of course, essential that the device be properly positioned in order that it can accomplish its desired function. It is also important that the device be properly positioned as quickly and expeditiously as possible. Due to the fact that the device extends into the patient, it is not possible to visually observe the positioning of the device. For this reason, it has become necessary to develop ways and means of determining the position of the intubating device within the patient.

One way of determining the position of the intubating device is to make the feeding tube of a radio-opaque material so that its position can be determined by X-ray or the like. This procedure is time consuming and subjects the patient to additional X-rays.

Another procedure for determining the position of the intubating device is to feed air through the feeding tube. The physician can then listen for the bubbling air with a stethoscope or the like and determine the position of the tube.

Another procedure for determining the position of the intubating device is to aspirate the stomach through the feeding tube and determine the contents by removing the contents with a syringe or the like.

The problem with the above procedures for determining the position of the intubating device is that most of these procedures require removal of the metal stylet before they can be carried out. If it is determined that the intubating device is improperly positioned then the stylet must be reinserted in the feeding tube. The reinsertion of the stylet may result in considerable discomfort and possible danger to the patient.

There are numerous prior art patents relating to intubating or naso-gastric devices including: Hargest U.S. Pat. No. 4,249,535; Stevens U.S. Pat. No. 3,503,385; Pezak U.S. Pat. No. 3,395,711; Guss U.S. Pat. No. 4,033,331: Fettel U.S. Pat. No. 3,896,815; Linder U.S. Pat. No. 3,957,055; Ring U.S. Pat. No. 3,964,488; Wallace U.S. Pat. No. 2,688,329; Dick U.S. Pat. No. 3,070,089.

Another United States patent of interest is the Waters U.S. Pat. No. 4,388,076, granted June 14, 1983. This patent purports to be directed to the problem of repositioning the intubating device in the event it is found to have been incorrectly positioned in the first instance.

This patent discloses a flexible feeding tube having discharge openings at one end. There is a metal stylet positioned in telescoping relationship within the feeding tube. The proximal end of the flexible feeding tube is attached to a connector which, in turn, is adapted to be connected to a syringe so that the syringe communicates with the interior of the flexible feeding tube. The metal stylet extends through the flexible tube and into the bore of the connector.

The terminal end of the metal stylet is formed into a hook which is positioned and secured within the passageway of the connector. The stylet is removed before the process of feeding liquid nourishment to the patient.

The positioning of the hook member is a task requiring a certain amount of manipulative skill and, with the stylet in this position, there is the possibility of clogging the passageway.

OBJECTS OF THE INVENTION

With the foregoing in mind, it is an object of this invention to provide a simple, easily constructed intubating device.

It is another object of this invention to provide a new and improved intubating device for positioning the intubating device and for supplying liquid nourishment to a patient.

Another object of this invention is to provide a new and improved intubating device wherein a flexible metal stylet is used to position a flexible tube which is secured to the connector so as not to obstruct the passageway through the connector.

A still further object of this invention is to provide a new and improved intubating device which can be manufactured and assembled simply and expeditiously.

Another object of this invention is to provide a new and improved intubating device having a flexible tube, a connector and a positioning stylet wherein the connector has an unobstructed passageway to the flexible tube.

A further object of this invention is to provide a new and improved intubating device having a flexible tube, a connector and a stylet wherein the stylet is embedded in the connector so that it does not interfere with the passage of liquids.

Additional objects and advantages of the invention will be set forth in the description which follows and, in part, will be obvious from the description; the objects and advantages being realized and attained by means of the instrumentation, parts, apparatus, elements and constructions particularly pointed out in the appended claims.

BRIEF DESCRIPTION OF THE INVENTION

Briefly described, the present invention relates to an intubating device comprising a flexible feeding tube adapted to convey nourishment to a human patient, and a Bolus tube or weight is in operative relationship with the flexible tube to position the same in operative relationship. There is a connector member, one end of which is adapted to be connected to a supply of nourishment such as a syringe. The other end of the connector is in communication with the flexible tube. The invention includes a stylet preferably made of metal, fixedly attached to the connector so that it can extend into the flexible feeding tube without extending into or blocking the passageway through the connector.

The invention consists of the novel parts, constructions and improvements shown and described.

The accompanying drawings which are incorporated in and constitute a part of this specification illustrate an embodiment of the invention and together with the description serve to explain the principles of the invention.

OF THE DRAWINGS

Figures 1, 2, 3:
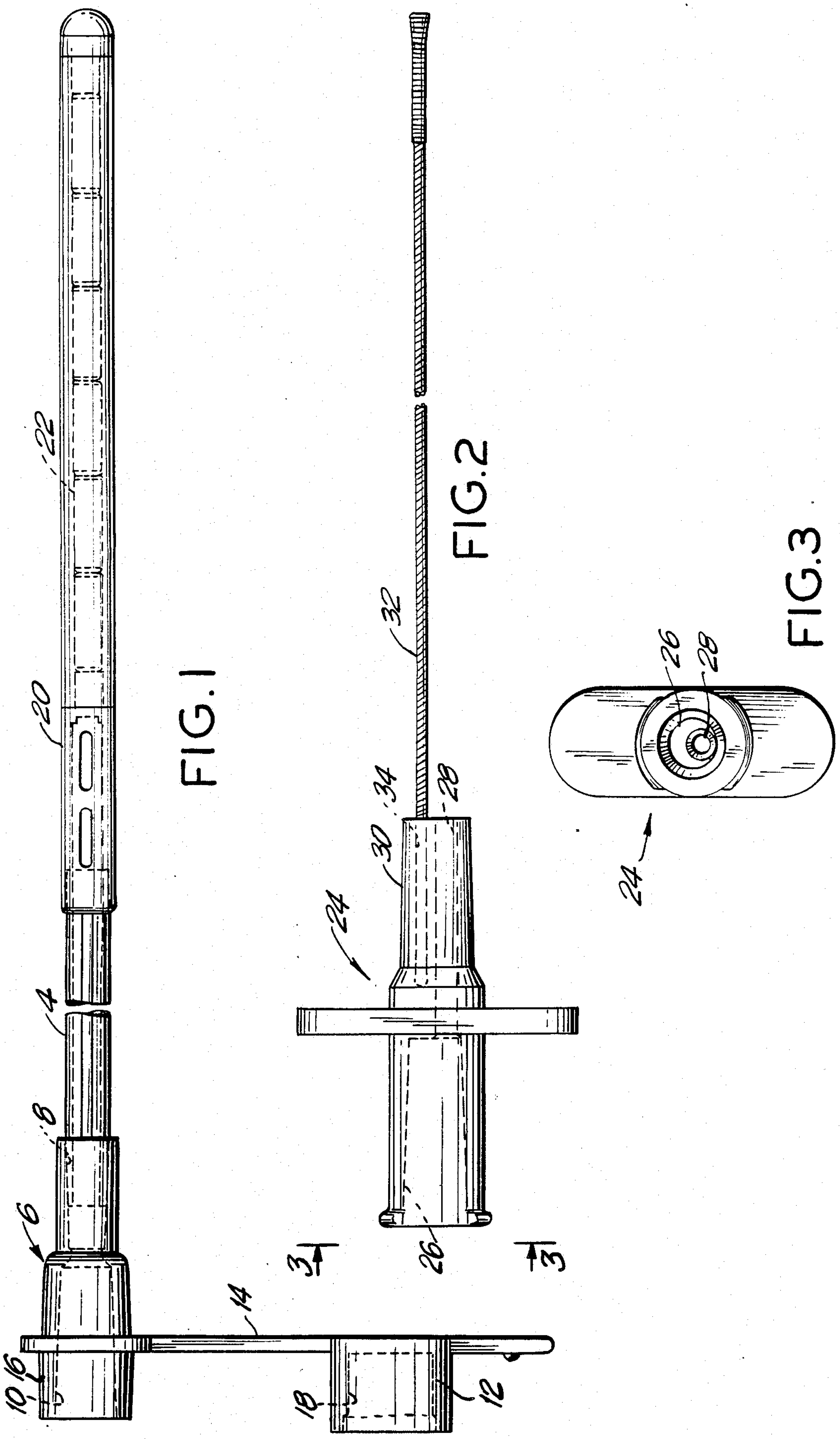
FIG. 1 is a plan view of the invention.
FIG. 2 is a side view of the stylet member of the present invention.
FIG. 3 is a sectional view of the invention taken along line 3—3 of FIG. 2.

Referring to the drawings, there is shown a flexible feeding tube 4 which can be made of some suitable plastic such as polyvinylchloride, polyethylene or polyurethane. The terminal end of the flexible feeding tube can have suitable openings for discharge of liquid nourishment passed through the tube.

There is a connector member 6 adapted to be connected at one end to a source of liquid nourishment, such as a syringe.

The other end of the connector member 6 is adapted to be connected to the flexible feeding tube 4. One end of the connector member 6 has a female recess 8 for receipt of the flexible feeding tube 4 and the other end of the tubular connector has a female recess 10 for receipt of the male member of the metal positioning stylet to be described subsequently.

For the purpose of closing the intubating device when not in use, the device is provided with a plug 12 attached to a flexible strap member 14. For this purpose the tube connector 6 has a male member 16 adapted to fit within the female recess 18. The terminal end of the flexible feeding tube 4 is in telescoping relationship with a bolus tube 20 having a plurality of small weights 22. The purpose of the Bolus tube and weights is to assist in positioning the feeding tube in the desired position within the patient. The Bolus tube and weights provided a degree of rigidity to the flexible feeding tube for this purpose.

In accordance with this invention, means is provided for insuring proper positioning of the flexible feeding tube within the patient. As embodied, this means includes a stylet holder 24 having a circular flange extending therefrom. This circular flange is used to position the device by hand manipulation. The stylet holder includes a female recess 26 at the terminal end adapted to receive a male tube or nozzle from a source of liquid nourishment such as a syringe or the like. Extending through the stylet is a fluid passageway 28. The purpose of the passageway 28 is threefold: It is used for supplying water as a lubricant; it is used to aspirate the stomach contents to determine positioning of the stylet; and it is used for ausculation to determine placement. The other end of the stylet holder includes a hub 30.

In accordance with this invention means is provided for connecting a metal stylet to the stylet holder in a permanent manner so as not to interfere with the flow of fluid for the purposes described above.

As embodied, this means includes a metal stylet consisting of a twisted metal wire 32. Conveniently, the wire is twisted so as to provide a rough outer surface. The hub member 30 has a blind hole 34 having a smaller inner diameter than the outer diameter of the metal stylet 32. The metal stylet is fixedly embedded in the blind hole 34 and the rough twisted surface of the metal stylet insures the fixed position of the stylet with respect to the stylet holder. With the metal stylet attached to the hub of the stylet in a position offset from the center of the stylet holder and the hub member, the stylet does not interfere with the flow of fluid through the passageway 28.

In use, the hub 30 of the stylet holder is placed within the female recess of the tube connector so that the metal stylet is positioned within the flexible tube to form an intubating assembly. The assembly is then placed within the human patient and manipulated until it is believed to be properly positioned. The patient is then aspirated by a syringe or the like and the contents analyzed to determine if the intubating assembly is properly positioned. If the intubating device is not properly positioned, it can be repositioned, without removing the stylet, and the procedure repeated until the intubating assembly is properly positioned.

After the device is properly positioned, the stylet is removed and liquid nourishment can be supplied to the patient in the usual manner.

What is claimed is:

1. An intubating device permitting aspiration of gastric juices to determine proper positioning of the device having a stylet which can be positioned within a human patient without removal of the stylet comprising:

a. a tube connector having connected at one end thereof a flexible feeding tube for conveying liquid nourishment to the patient and having an opening at the other end;

b. a stylet holder having a circular flange portion extending from the stylet holder for hand manipulation of the stylet holder and an opening at one end of the stylet holder for receipt of a supply of liquid nourishment;

c. a hub at the other end of said stylet holder extending from said circular flange;

d. a blind hole in said hub extending from the end of said hub towards said circular flange, said hole being offset from the center of said hub;

e. a fluid passageway extending through said stylet holder;

f. a metal stylet fixedly embedded in said blind hole and extending therefrom and forming a one-piece unit with said hub;

g. said stylet holder and stylet adapted to be positioned in telescoping relationship with said tube connector and said feeding tube with the fluid passageway unobstructed by said stylet;

h. whereby when the intubating device is initially positioned an aspiration process can be accomplished through the unobstructed fluid passageway and after the device is properly positioned liquid nourishment can flow unobstructed through said passageway.

2. A device as defined in claim 1 wherein said metal stylet has a rough exterior surface and a diameter greater than the diameter of said blind hole.

3. A device as defined in claim 2 wherein said metal stylet is a twisted wire.

* * * * *